United States Patent
Laghi et al.

(10) Patent No.: US 10,966,845 B2
(45) Date of Patent: Apr. 6, 2021

(54) KNIT PROSTHETIC LINER TEXTILE WITH DIFFERENTIATED KNIT FABRIC EXTERIOR

(71) Applicant: Alps South Europe S.R.O., Plzeň (CZ)

(72) Inventors: Aldo Laghi, Pinellas Park, FL (US); Nathaniel Vint, Oldsmar, FL (US)

(73) Assignee: Alps South Europe, S.R.O., Plzen (CZ)

( * ) Notice: Subject to any disclaimer, the term of this patent is extended or adjusted under 35 U.S.C. 154(b) by 52 days.

(21) Appl. No.: 16/120,929

(22) Filed: Sep. 4, 2018

(65) Prior Publication Data

US 2019/0070024 A1 Mar. 7, 2019

Related U.S. Application Data

(60) Provisional application No. 62/554,102, filed on Sep. 5, 2017.

(51) Int. Cl.
| | | |
|---|---|---|
| *A61F 2/78* | (2006.01) | |
| *A61F 2/80* | (2006.01) | |
| *A61F 2/50* | (2006.01) | |
| *A61F 2/60* | (2006.01) | |

(52) U.S. Cl.
CPC .............. *A61F 2/7812* (2013.01); *A61F 2/80* (2013.01); *A61F 2/5044* (2013.01); *A61F 2002/501* (2013.01); *A61F 2002/608* (2013.01); *A61F 2002/7818* (2013.01); *A61F 2002/7875* (2013.01)

(58) Field of Classification Search
CPC .... A61F 2/7812; A61F 2/80; A61F 2002/608; A61F 2002/7818; A61F 2002/501
See application file for complete search history.

(56) References Cited

U.S. PATENT DOCUMENTS

| | | | |
|---|---|---|---|
| 5,443,525 A | 8/1995 | Laghi | |
| 5,507,234 A | 4/1996 | Thorsen | |
| 5,728,168 A | 3/1998 | Laghi | |
| 6,454,812 B1 | 9/2002 | Laghi | |
| 6,544,292 B1 | 4/2003 | Laghi | |
| 6,764,631 B1 | 7/2004 | Laghi | |
| 8,317,873 B2 * | 11/2012 | Doddroe | A61F 2/7812 623/36 |
| 9,216,099 B2 * | 12/2015 | Laghi | A61F 2/7812 |
| 2005/0240283 A1 | 10/2005 | Kania | |

(Continued)

FOREIGN PATENT DOCUMENTS

EP 2674134 A1 12/2013

*Primary Examiner* — Brian A Dukert
*Assistant Examiner* — Amanda M Barkan
(74) *Attorney, Agent, or Firm* — GrayRobinson, P.A.

(57) ABSTRACT

A prosthetic liner for use with a prosthetic assembly that acts as the interface between the residual limb of an amputee and the socket assembly. The prosthetic liner comprises an outer textile with variable stretch characteristics due to the knit construction and stitching and an interior gel layer. The distal region of the liner textile has less stretch than does the intermediate region or proximal region and is stitched together to form a unitary liner. The liner advantageously minimizes a condition referred to as "pistoning" wherein the distal most portion of the residual limb ascends and descends in the lower portion of the socket creating an unhealthy condition for the residual limb.

11 Claims, 11 Drawing Sheets

(56) References Cited

U.S. PATENT DOCUMENTS

2007/0162153 A1* 7/2007 Barnes .................. A61F 2/78
                                                    623/36
2011/0208321 A1   8/2011 Doddroe et al.
2014/0249650 A1   9/2014 Laghi et al.

* cited by examiner

KNIT PROSTHETIC LINER TEXTILE WITH DIFFERENTIATED KNIT FABRIC EXTERIOR

CROSS-REFERENCE TO RELATED APPLICATIONS

This application claims priority to provisional application No. 62/554,102 filed Sep. 5, 2017, the disclosure of which is hereby incorporated by reference herein.

BACKGROUND OF THE INVENTION

Field of the Invention

This invention relates to liners for use in a prosthetic assembly. More particularly, the described invention relates to liners having a particular stitching such that the distal end of the liner has less stretch than the proximal end of the liner so as to reduce pistoning.

Description of the Background Art

Prosthetic liners have been in use since the 1970's, mostly custom made, and made of various materials. Silicone liners, without a fabric cover, were developed in the late 1980s and became widely used as of the 1990s. During that time, the first versions of fabric covered liners were developed.

The liners disclosed in U.S. Pat. Nos. 5,443,525, 5,507,234, 5,728,168, 6,544,292, and 6,764,631 each represent advances in the field of fabric covered liners and the disclosures of which are hereby incorporated by reference. Additionally, U.S. Pat. No. 6,454,812, also hereby incorporated by reference, describes a liner comprising additional features attached to the liner textile to limit the vertical stretch at the distal end of a liner and is incorporated herein by reference. This method has been used successfully within the field of prosthetics to provide the liner textile with a strengthened distal end, means for attaching a threaded mechanical feature, and a boundary layer that prevents the thermoplastic elastomer from undesirably passing through the textile during high pressure processing.

Fabric liners having a lower longitudinal elongation at the distal end were initially popular because they prevented "pistoning." Pistoning is the loss of suspension of a residual limb when weight is taken off of it and the resulting pushing down of the limb on the socket when weight is applied, like the piston of car. This means that every time the amputee attempted to move his/her leg, there would be a delay between when the residual limb moved and when the prosthesis moved. Pistoning is more pronounced in locking liners, i.e. liners that attach the prosthesis to the residual limb by means of a distal umbrella and distal pin with a corresponding lock. Older versions of fabric liners with lower longitudinal elongation at the distal end prevent pistoning but also constrain the knee flexion of the amputee. If a liner exhibits a high longitudinal elongation throughout its length, then the prosthesis will move up and down during ambulation. On the other hand, if there is no longitudinal elongation then the amputee will find it difficult to flex the knee.

In order to overcome this issue, liners with a distal matrix were developed such as the liner described in U.S. Pat. No. 6,454,812, described above. These liners include an additional fabric matrix which is knit to minimal longitudinal elongation where the matrix is bonded to the interior of the external fabric of the liner. However, this construction is expensive to construct due to the fact that the additional steps of applying adhesive to the interior of the exterior fabric, applying the reinforcing matrix to the adhesive layer, and curing of the adhesive are required. The present invention overcomes this problem by eliminating the reinforcing matrix and replaces it with a differentiated knitting of the exterior fabric.

The present invention utilizes stitching with reduced stretch regions such that the distal end of the liner has less stretch than the proximal end so as to prevent pistoning.

Therefore, it is an object of this invention to provide an improvement which overcomes the aforementioned inadequacies of the prior art devices and provides an improvement which is a significant contribution to the advancement of the liner art.

Another object of the invention is to provide a liner for prosthetic assemblies that reduces pistoning of the residual limb when in use.

Another object of the invention is to provide a liner for prosthetic assemblies that can also be used with a locking prosthetic assembly.

Another object of the invention is to provide a liner that implements two or more stitching types.

Another object of the invention is to provide a liner with less stretch capability at the distal end than at the proximal end.

Another object of the invention is to provide a liner with variable stretch characteristics based on knit construction and stitching.

The foregoing has outlined some of the pertinent objects of the invention. These objects should be construed to be merely illustrative of some of the more prominent features and applications of the intended invention. Many other beneficial results can be attained by applying the disclosed invention in a different manner or modifying the invention within the scope of the disclosure. Accordingly, other objects and a fuller understanding of the invention may be had by referring to the summary of the invention and the detailed description of the preferred embodiment in addition to the scope of the invention defined by the claims taken in conjunction with the accompanying drawings.

SUMMARY OF THE INVENTION

The present invention relates generally to a liner for use in a prosthetic assembly having variable stretch regions at a distal end providing different stretch regions.

Specifically, the present invention relates to a prosthetic liner having a lower longitudinal stretch in the distal region than in either the proximal or optional intermediate region. The distal region may stretch anywhere from 0-30% vertically and 10-200% horizontally as compared to the proximal region's vertical stretch of 55-125% and 100-175% horizontally. The stretch of the liner at various pressure sensitive regions of a residual limb can also be lowered or heightened depending on the area. A variety of stitches may be used at the distal end to implement this lowered longitudinal stretch. Preferably, the liner is made of a stretchable material. The liner also has an interior layer of elastomer gel. The design of this prosthetic liner is primarily to prevent the "pistoning" of the amputee's residual limb within the liner and for comfort over pressure-sensitive areas of the residual limb.

The foregoing has outlined rather broadly the more pertinent and important features of the present invention in order that the detailed description of the invention that follows may be better understood so that the present contribution to the art can be more fully appreciated. Additional features of the invention will be described hereinafter which form the subject of the claims of the invention. It should be appreciated by those skilled in the art that the conception and the specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims.

BRIEF DESCRIPTION OF THE DRAWINGS

For a more complete understanding of the present disclosure and its advantages, reference is now made to the following descriptions, taken in conjunction with the accompanying drawings, in which.

Similar reference numerals refer to similar parts throughout the several views of the drawings.

DETAILED DESCRIPTION OF THE PREFERRED EMBODIMENT

The following description is of the best mode presently contemplated for carrying out the invention. This description is not to be taken in a limiting sense, but is made merely for the purpose of describing one or more preferred embodiments of the invention. The scope of the invention should be determined with reference to the claims.

Figure 1:
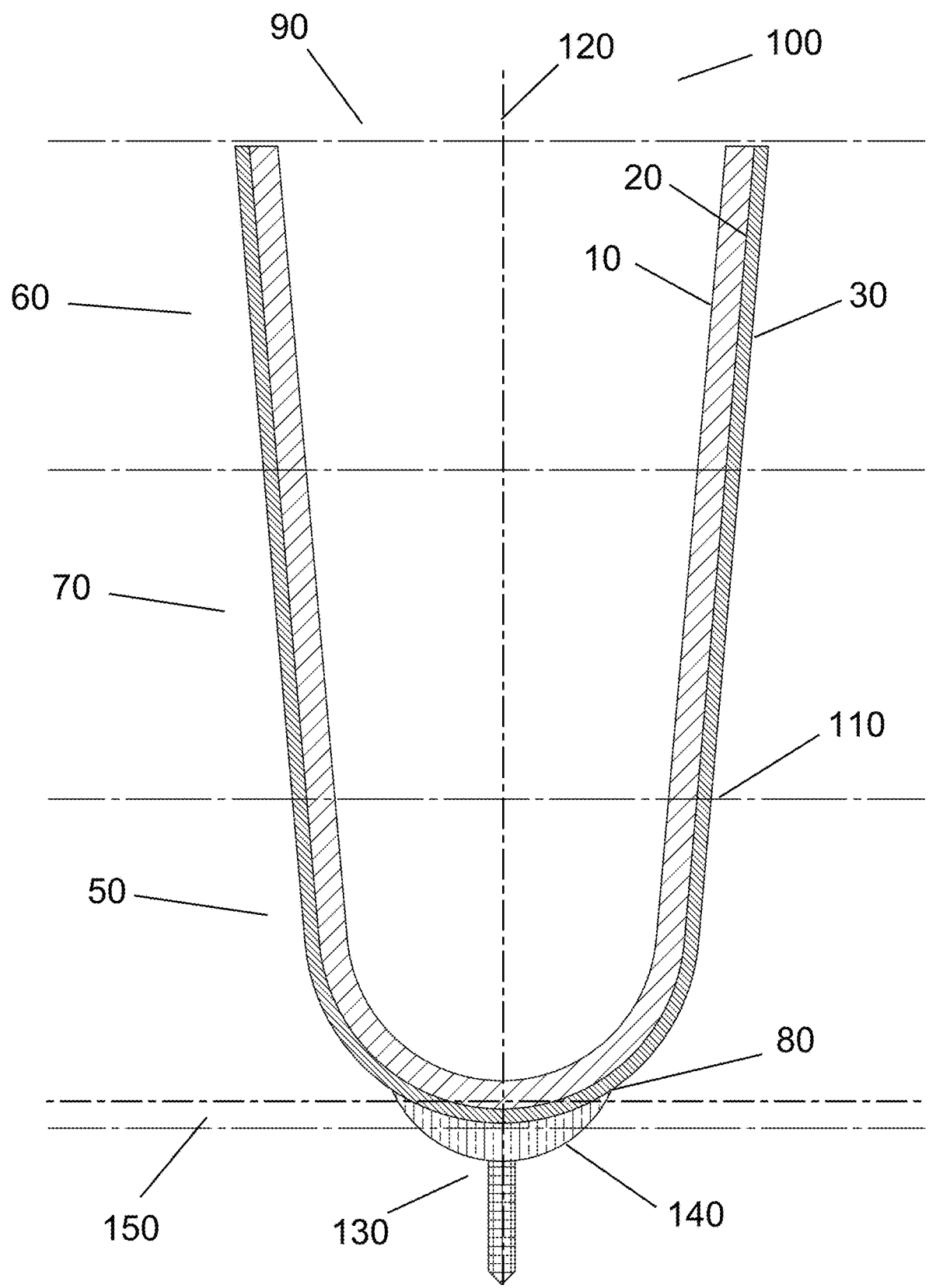
FIG. 1 is a cross-sectional view of the present invention for use with a locking prosthetic assembly comprising two different types of stitches showing the different relevant regions.

The present invention relates to a liner 100 for use with prosthetic devices. As shown in FIG. 1, the liner 100 for use with a prosthetic assembly comprises a plurality of types of stitching. The liner 100 comprises a distal region 50, proximal region 60, and an optional intermediate region 70. In one embodiment, the distal region 50 that comprises the distal end 80 of the liner is constructed with a reduced vertical stretch when compared to the upper region 60 of the liner. Preferably, the distal region 80 has a vertical stretch of 0-30% and a horizontal stretch of 10-200% as compared to the proximal region 60, which preferably has a vertical stretch of 55-125% and a horizontal stretch of 100-175%. Optionally, the intermediate region 70 may have a vertical stretch of 15-40% and a horizontal stretch of 80-120% or it may have the same stretch characteristics of the proximal region 60. The reduced stretch of the distal region 50 is achieved on a flatbed knitting machine by use of a variety of different stitches as described below. In a preferred embodiment, the liner 100 is knit in a single piece construction with the proximal end 90 being open and the distal end 80 being closed. Alternatively, the two halves may be independently constructed and then sewn or attached together by another means to form the completed liner textile.

Preferably, the liner 100 is knit using computerized flatbed knitting machines that allow the use of several different yarns at the same time or sequentially in the same garment, including elastomeric fibers such as LYCRA®, latex, and silicone among others. These machines also allow the use of different stitch types in different areas of the same garment and controls the tension of each yarn being knitted. Further, an interior gel layer 10 resides on an interior surface 20 of exterior fabric layer 30. The gel layer 10 may be any form of stretchable elastomer as known in the industry or later developed but is preferably a styrene-based polymer.

In another embodiment, the liner 100 comprises regions of differing horizontal and vertical stretch stitching depending on anatomical features related to the residual limb or mechanical features related to the prosthetic socket. This means that the boundary 110 between the distal region 50 and the proximal region 60 (or intermediate region 70 if present) may shift location. The boundary 110 is preferably generally perpendicular to the central axis 120 of the liner 100. Additionally, the distal end 80 may house a locking mechanism 130. The use of a locking mechanism 130 requires a construction that is strong enough for the umbrella 140 to be retained by the fabric or else a catastrophic failure of the prosthesis may result. Typically, such locking mechanisms 130 are secured to the fabric through the use of a grommet that bites into the fabric or other similar means of attachment. In order for the fabric to withstand the localized stress imparted by the grommet, the construction of the knit at the distal end must be heavier and stronger than the rest of the fabric cover. Such construction cannot be used in the intermediate region 70 or proximal region 60 because it would impart poor functionality to the liner and limit the user's movement.

More specifically, the fabric in the locking mechanism region 150 must have little to no longitudinal elongation but high circumferential elongation in order to comfortably accommodate the residual limb. The locking mechanism region 150 is limited to the area juxtaposed to the locking mechanism 130. The thickness of the fabric in the locking mechanism region 150 should greater than the thickness of the fabric in the distal region 50. The distal region 50, as compared to the locking mechanism region 150, must have a greater degree of longitudinal elongation in order to facilitate knee flexion. The intermediate region 70 may have an even greater degree of longitudinal elongation and circumferential elongation than the distal region 50 to provide greater comfort to the amputee when sitting or moving.

Figure 2:
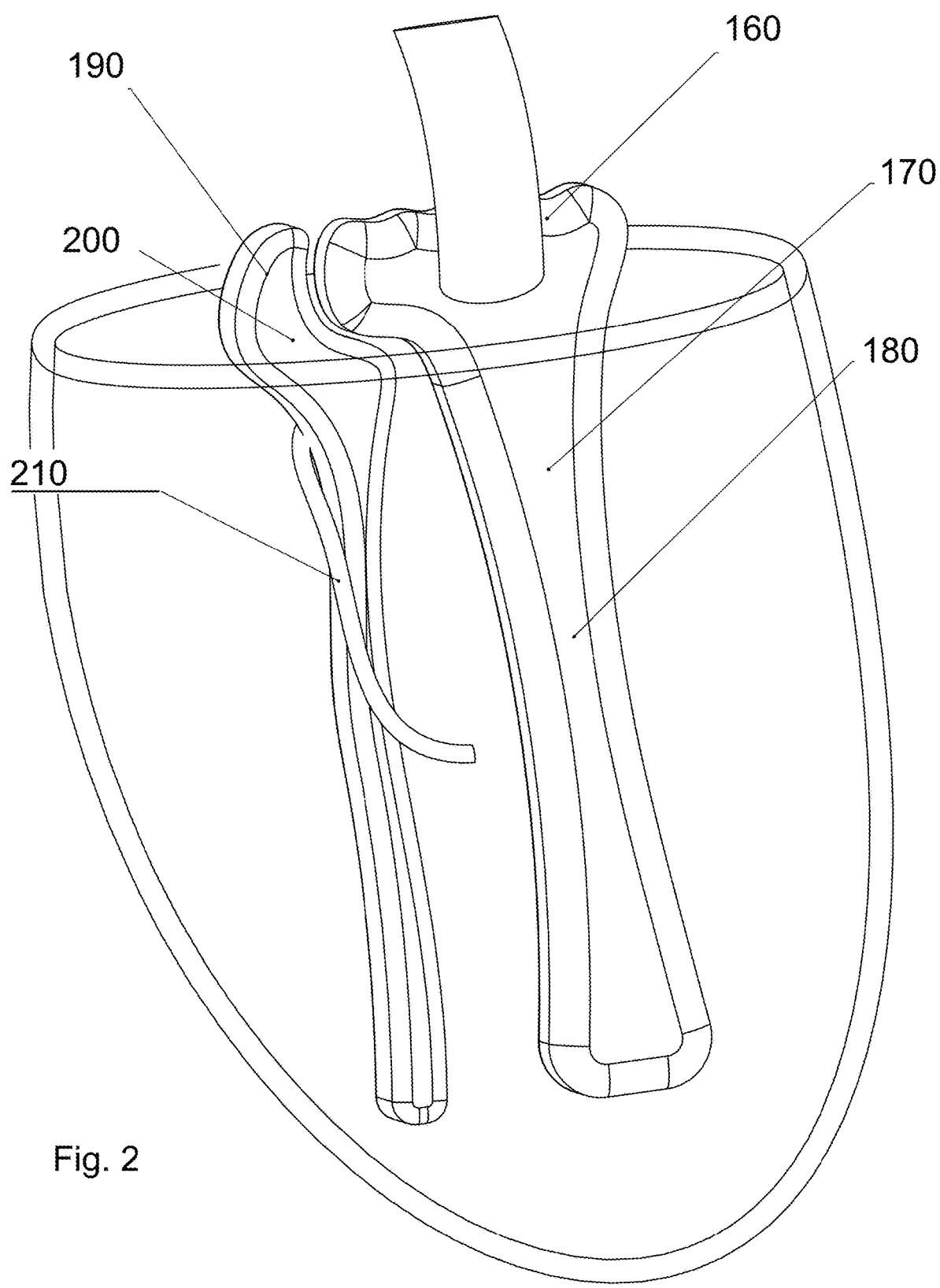
FIG. 2 is a cross-sectional view of the present invention showing below-the-knee amputation pressure sensitive areas.
Figure 3:
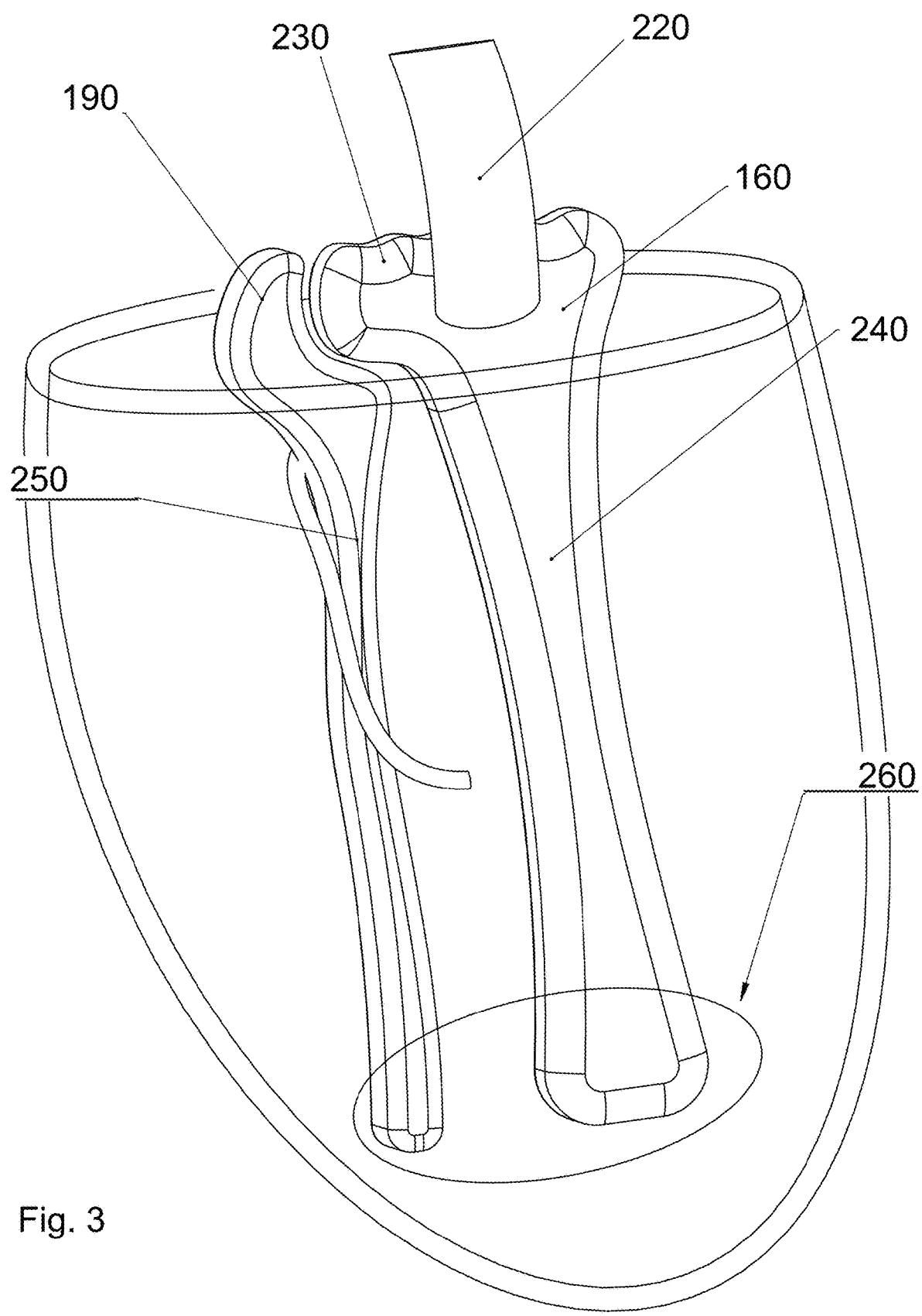
FIG. 3 is a cross-sectional view of the present invention showing below-the-knee-amputation pressure tolerant areas.

In another embodiment, the liner textile comprises regions of differing horizontal and vertical stretch depending on anatomical features related to the residual limb or mechanical features related to the prosthetic socket. There are various areas of the lower limbs that are more pressure sensitive, requiring more elongation, and various areas that are more pressure tolerant, which require less elongation. As shown in FIG. 2, the pressure sensitive areas for below-the-knee amputations comprise the portions of the tibia 160 such as the anterior tibia 170 and the anterior tibial crest 180 as well as parts of the fibula 190 such as the fibular head and neck 200, and the fibular nerve 210. These regions of the body exhibit sensitivity to pressure and therefore require a liner having greater longitudinal or circumferential elongation at those points. On the other hand, as shown in FIG. 3, the pressure-tolerant areas for below-the-knee amputations comprise the patellar tendon 220, the medial tibia plateau 230, the tibial shaft 240, the fibular shaft 250, and the distal end 260 of tibia 160 and fibula 190. These regions may have more restricted longitudinal or circumferential elongation due to the tolerance these regions exhibit.

Figure 4:
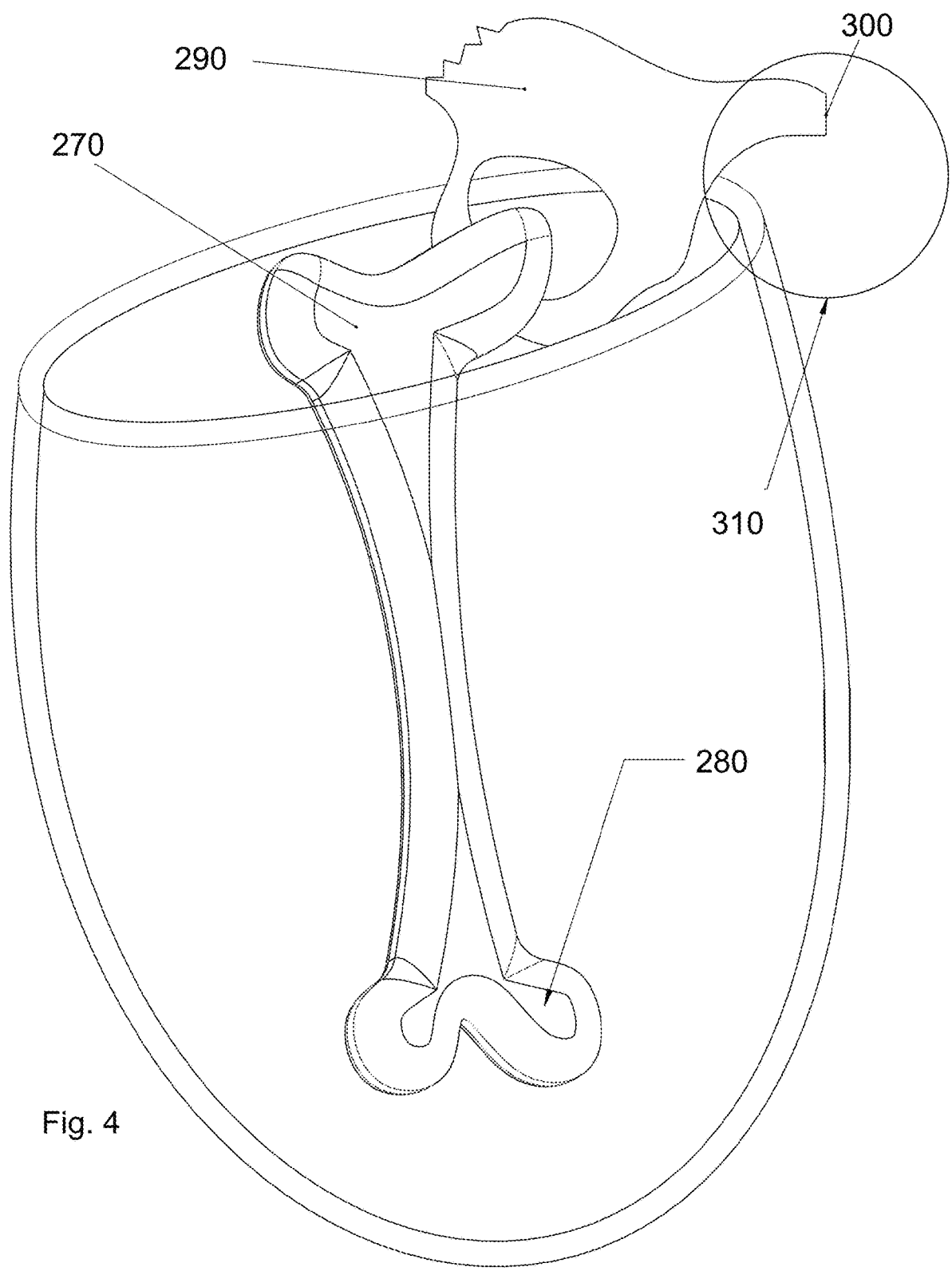
FIG. 4 is a cross-sectional view of the present invention showing above-the-knee amputation pressure sensitive areas.
Figure 5:
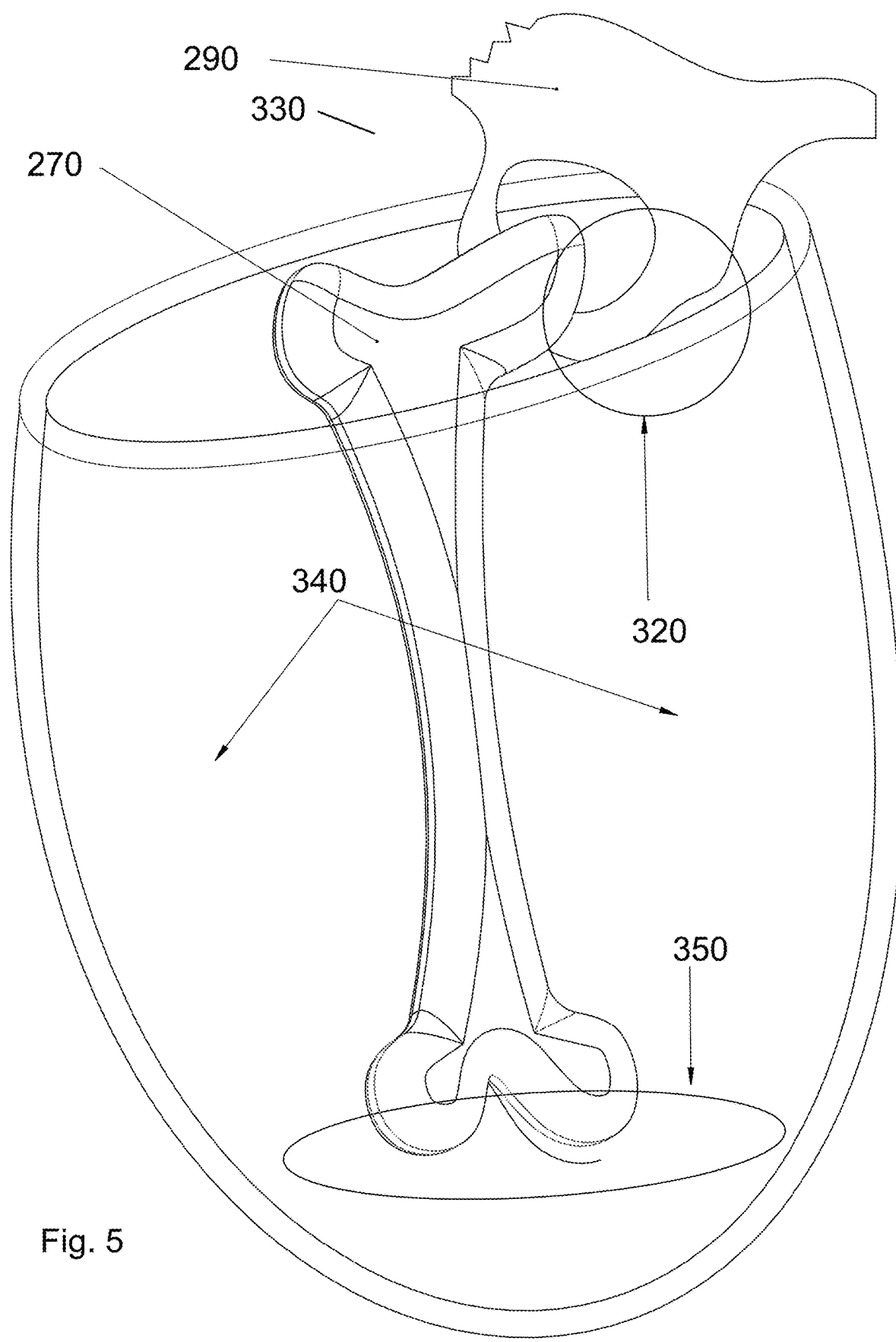
FIG. 5 is a cross sectional view of the present invention showing above-the-knee amputation pressure tolerant areas.

Similarly, as shown in FIGS. 4 and 5, above-the-knee amputations have similarly pressure sensitive and pressure tolerant areas. The pressure sensitive areas comprise the distolateral end 280 of the femur 270, the pubic symphysis 300 of the pelvic bone 290, and the perineal area 310. The pressure tolerant areas comprise the ischial tuberosity 320 of the pelvic bone 290, the gluteals 330, the lateral sides 340 of the residual limb, and the distal end 350 of the femur 270. As with below-the-knee, pressure sensitive areas of above-the-knee amputations require greater longitudinal or circumferential elongation at those points while the pressure tolerant areas may have more restricted longitudinal or circumferential elongation due to the tolerance those regions exhibit.

Figure 6A:
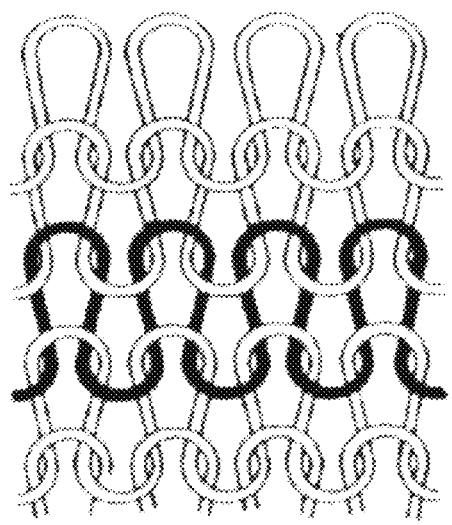
FIGS. 6A-6N are various stitching types that can be used in the distal region of the present invention to prevent pistoning.
Figure 6B:
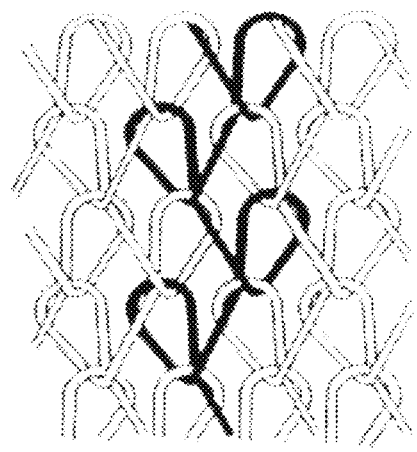
Figure 6C:
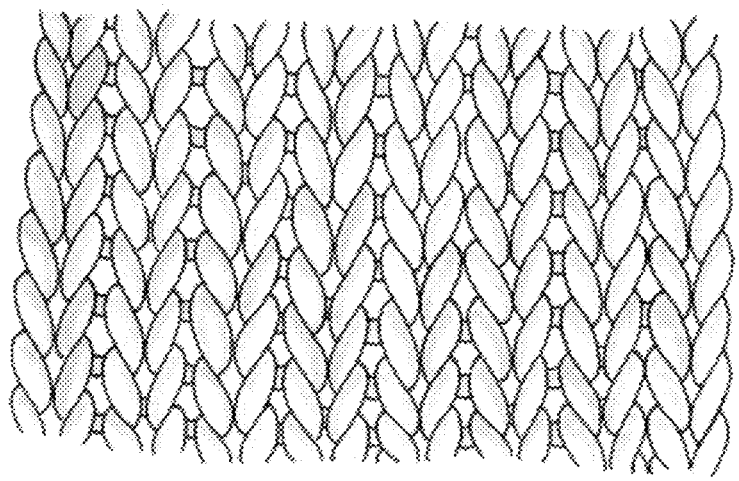
Figure 6D:
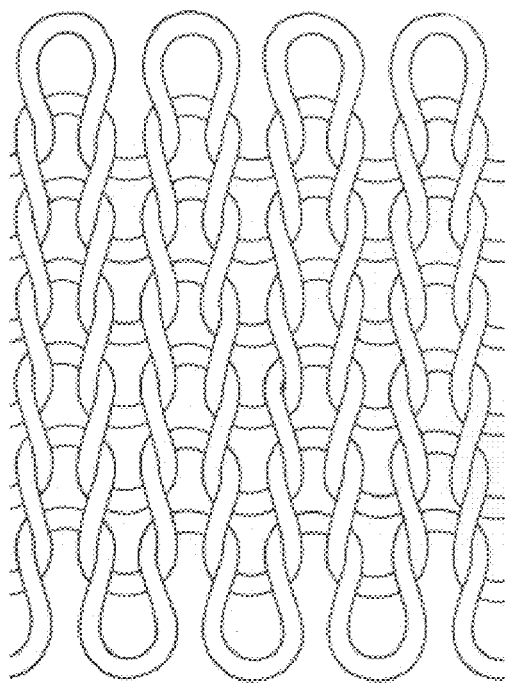
Figure 6E:
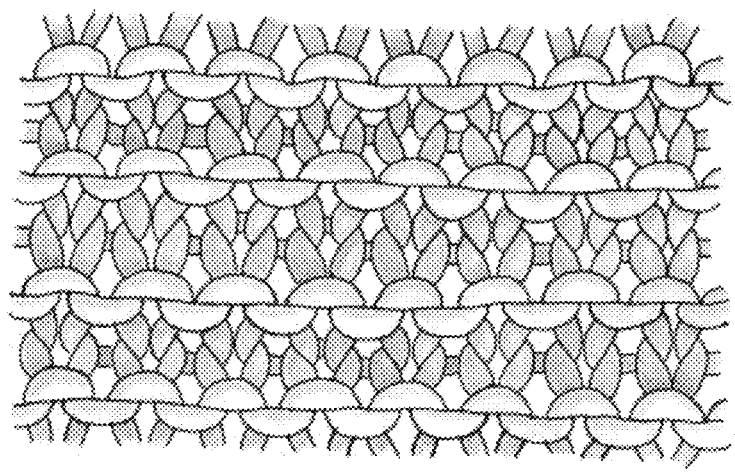
Figure 6F:
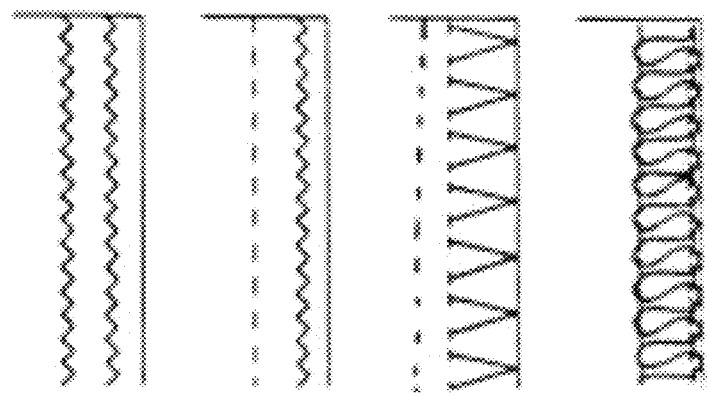
Figure 6G:
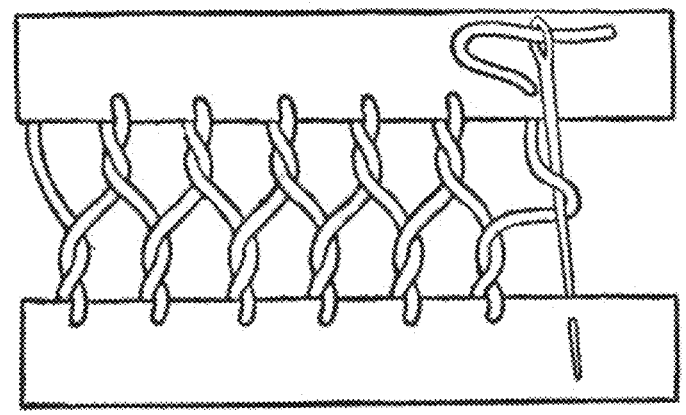
Figure 6H:
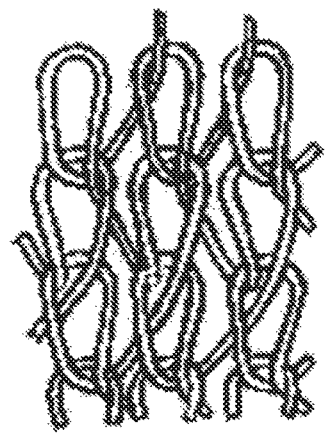
Figure 6I:
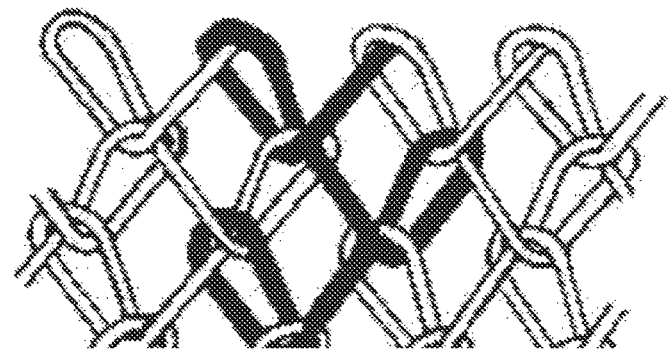
Figure 6J:
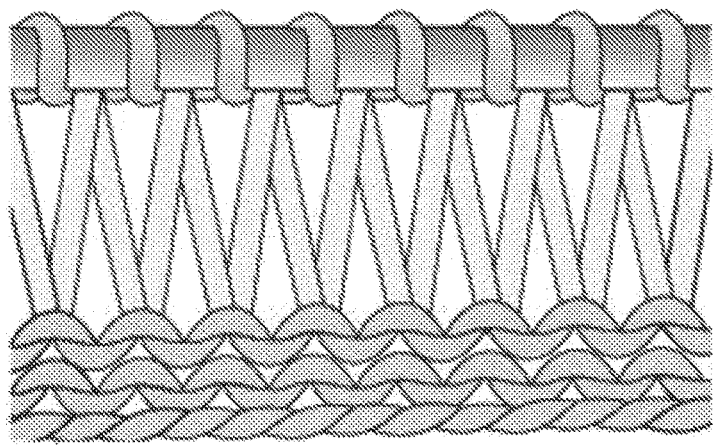
Figure 6K:
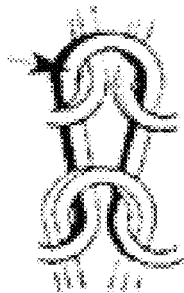
Figure 6K:
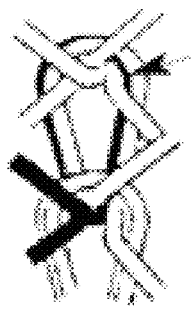
Figure 6L:
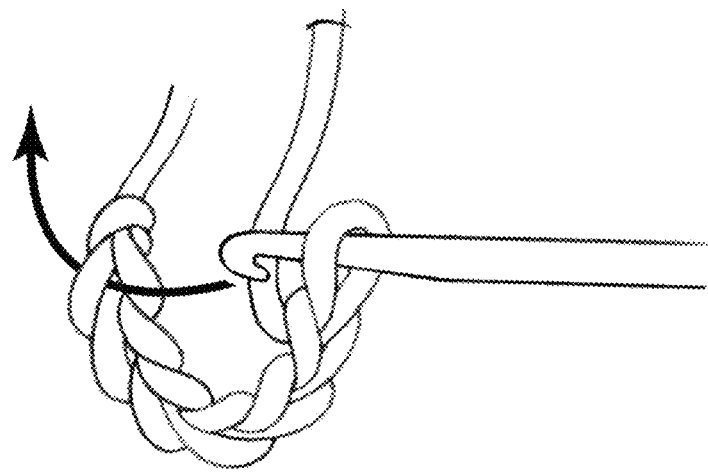
Figure 6M:
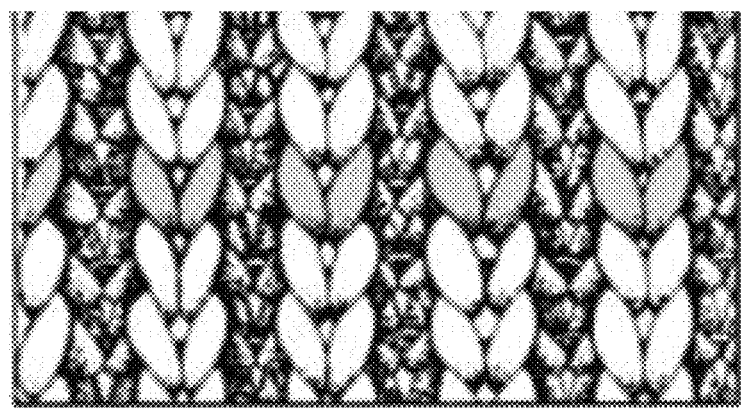
Figure 6N:
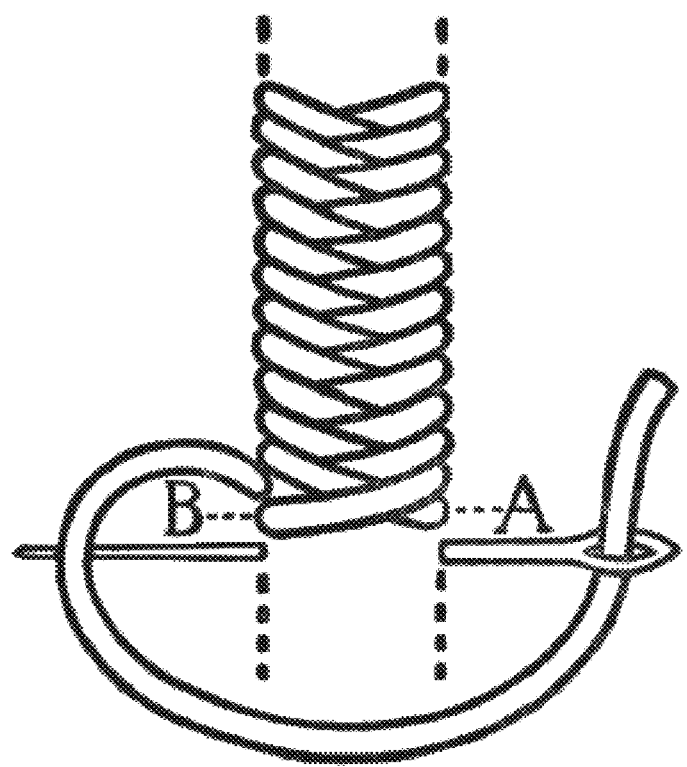

The fabric of the liner can be constructed in a number of ways so as to provide the required functionality. The functionality can be altered by using different yarns or deniers, different elastomers, different weights of elastomers, and different stitches, among other ways, to provide the right longitudinal and circumferential elongation along the length of the liner. Typical yarn types include, but are not limited to, polyester, nylon, acrylic, cellulosic, aramid, natural fibers, and metal wires. Typical elastomers include LYCRA®/polyurethane, natural rubber, nitrile, and silicone. Typical stitch types, as shown in FIGS. 6A-6N, include weft (FIG. 6A), warp (FIG. 6B), stockinette (FIGS. 6C and 6D), garter (FIG. 6E), seam (FIG. 6F), fagoting (FIG. 6G), tricot (FIGS. 6H and 6I), elongated (FIG. 6J), plated (FIG. 6K), slip (FIG. 6L), dip (FIG. 6M), and basket (FIG. 6N) and are used solely in the distal region 50 of the liner 100 so as to differentiate the elongation found in the proximal region 60.

The present disclosure includes that contained in the appended claims, as well as that of the foregoing description. Although this invention has been described in its preferred form with a certain degree of particularity, it is understood that the present disclosure of the preferred form has been made only by way of example and that numerous changes in the details of construction and the combination and arrangement of parts may be resorted to without departing from the spirit and scope of the invention.

Now that the invention has been described,

What is claimed is:

1. A prosthetic liner comprising:
   a fabric covering having an open proximal end and a closed distal end knit into a tubular shape, said fabric covering further comprising a proximal region and a distal region wherein said distal region has lower longitudinal elongation than said proximal region using a stitching selected from the group consisting of weft, warp, garter, seam, fagoting, tricot, elongated, plated, slip, dip, or basket stitches;
   wherein the distal region stretches 0-30% vertically and 10-200% horizontally and wherein the proximal region stretches 55-125% vertically and 100-175% horizontally;
   a locking mechanism region below said distal region housing a locking mechanism wherein said fabric covering in said locking mechanism region is thicker than said fabric covering in said distal region; and
   an elastomeric gel layer residing on an interior surface of said fabric covering.

2. The prosthetic liner of claim 1 wherein said fabric covering exhibits greater longitudinal elongation in pressure sensitive areas of a residual limb selected from the group consisting of an anterior tibia, an anterior tibial crest, a fibular head, a fibular neck, and a fibular nerve.

3. The prosthetic liner of claim 1 wherein said fabric covering exhibits lower longitudinal elongation in pressure tolerant areas of a residual limb selected from the group consisting of a patellar tendon, a medial tibia plateau, a tibial shaft, a fibular shaft, a distal end of a tibia, and a distal end of a fibula.

4. The prosthetic liner of claim 1 wherein said distal region can stretch from 0-30% vertically and 10-200% horizontally.

5. The prosthetic liner of claim 1 wherein said elastomeric gel layer comprises a styrene-based polymer.

6. A prosthetic liner having varying elongation characteristics comprising:
   a tubular fabric covering having an open proximal end and a closed distal end for housing a residual limb, said fabric covering further comprising:
   a proximal region and a distal region wherein said distal region is stitched differently than said proximal region using a stitching selected from the group consisting of weft, warp, garter, seam, fagoting, tricot, elongated, plated, slip, dip, or basket stitches;
   a locking mechanism region below said distal region housing a locking mechanism wherein said fabric covering in said locking mechanism region is thicker than said fabric covering in said distal region; and
   a styrene-based elastomeric gel layer residing on an interior surface of said fabric covering;
   wherein said distal region can stretch from 0-30% vertically and 10-200% horizontally and said proximal region can stretch from 55-125% vertically and 100-175% horizontally.

7. A prosthetic liner comprising:
   a fabric covering having an open proximal end and a closed distal end knit into a tubular shape, said fabric covering further comprising a proximal region and a distal region wherein said distal region is stitched such that said distal region has a longitudinal elongation of 0-30% and is stitched differently than said proximal region such that said proximal region has a longitudinal elongation of 55-125%, wherein said distal region further comprises stitching selected from the group consisting of weft, warp, garter, seam, fagoting, tricot, elongated, plated, slip, dip, or basket stitches;
   a locking mechanism region below said distal region housing a locking mechanism wherein said fabric covering in said locking mechanism region is thicker than said fabric covering in said distal region; and
   an elastomeric gel layer residing on an interior surface of said fabric covering.

8. The prosthetic liner of claim 7 wherein said proximal region has a greater longitudinal elongation than the distal region.

9. The prosthetic liner of claim 7 wherein said fabric covering exhibits greater longitudinal elongation in pressure sensitive areas of a residual limb selected from the group consisting of an anterior tibia, an anterior tibial crest, a fibular head, a fibular neck, and a fibular nerve.

10. The prosthetic liner of claim 7 wherein said fabric covering exhibits lower longitudinal elongation in pressure tolerant areas of a residual limb selected from the group consisting of a patellar tendon, a medial tibia plateau, a tibial shaft, a fibular shaft, a distal end of a tibia, and a distal end of a fibula.

11. The prosthetic liner of claim 7 wherein said elastomeric gel layer comprises a styrene-based polymer.

\* \* \* \* \*